United States Patent [19]
Oda et al.

[11] Patent Number: 5,250,966
[45] Date of Patent: Oct. 5, 1993

[54] OPHTHALMIC PHOTOGRAPHING APPARATUS HAVING A DISPLACEMENT MEASUREMENT UNIT

[75] Inventors: Haruo Oda, Yokohama; Eiji Satake, Machida; Ken Tomioka, Zushi, all of Japan

[73] Assignee: Nikon Corporation, Tokyo, Japan

[21] Appl. No.: 851,479

[22] Filed: Mar. 13, 1992

[30] Foreign Application Priority Data

May 10, 1991 [JP] Japan .................... 3-105813

[51] Int. Cl.$^5$ .............................. A61B 3/14
[52] U.S. Cl. ....................... 351/208; 351/206; 351/207; 354/62
[58] Field of Search ............... 351/208, 207, 206, 221, 351/212; 354/62

[56] References Cited

U.S. PATENT DOCUMENTS 4,756,613  7/1988  Okashita .................. 351/206
4,950,068  8/1990  Mizuta .................... 351/208

FOREIGN PATENT DOCUMENTS 56-72841  6/1981  Japan .

Primary Examiner—Martin Lerner
Assistant Examiner—Hung X. Dang
Attorney, Agent, or Firm—Shapiro and Shapiro

[57] ABSTRACT

An ophthalmic photographing apparatus comprises an illumination optical system for illuminating an eye to be tested, a viewing optical system having a variable magnification optical system for viewing the illuminated eye to be tested, and a photographing device detachably mounted on the viewing optical system. A position change of a predetermined part due to the change of magnification of the variable magnification optical system is measured to produce a signal representing the displacement. The signal representing the magnification of the variable magnification optical system is used to control an intensity of a flash light.

12 Claims, 4 Drawing Sheets

OPHTHALMIC PHOTOGRAPHING APPARATUS HAVING A DISPLACEMENT MEASUREMENT UNIT

BACKGROUND OF THE INVENTION

1. Field of the Invention

The present invention relates to an ophthalmic photographing apparatus for illuminating an eye to be tested, observing it and photographing it.

2. Related Background Art

In a prior art ophthalmic photographing apparatus such as a slit lamp microscope, a compact construction is needed for clinical examination. Accordingly, in order to enhance the operability in the clinical examination, not only a camera but also a photographic recorder may be removably attached to a monitoring microscope of the ophthalmic photographing apparatus so that it may be used as a clinical slit lamp when it is not used for photographing. Because of such a construction, the ophthalmic photographing apparatus such as the slit ramp microscope usually does not have an exposure determination unit. Thus, a user experimentarily determines the exposure by his/her decision based on an area to be photographed and a magnification. As a result, proper exposure is difficult to attain. Recently, an ophthalmic photographing apparatus which detects a photographing magnification and other photographing condition and calculates proper exposure has been proposed as disclosed in Japanese Laid-Open Patent Application No. 56-72841, an ophthalmic photographing apparatus which detects the magnification and calculates the proper exposure is now commercially available.

In the prior art ophthalmic photographing apparatus which detects the photographing magnification and other photographing conditions and calculates the proper exposure, it is required to built in a detection unit for a magnification signal. As a result, the apparatus is of large size and it is exclusively used for photographing because the photographing apparatus is fixed and it cannot be used for clinical examination.

When the photographing apparatus is detachable in order to enhance the operability in the clinical examination, electrical contacts are formed in a mount. Thus, the attachment and detachment of the photographic recorder are difficult to attain because of the contact pressures, and the contacts are apt to be deteriorated.

SUMMARY OF THE INVENTION

In the light of the above, it is an object of the present invention to provide an ophthalmic photographing apparatus which can attain proper exposure while enhancing the operability in the clinic examination.

The ophthalmic photographing apparatus of the present invention comprises:

an illumination optical system for illuminating an eye to be tested;

a viewing optical system having a variable magnification optical system for viewing the illuminated eye to be tested;

a photographing device detachably mounted on the viewing optical system;

displacement measurement means for measuring a displacement of a predetermined part due to the change of magnification of said variable magnification optical system; and signal output means for outputting a signal representing the displacement measured by the displacement measurement means.

The variable magnification optical system in the present invention may be a continuously variable magnification optical system which can continuously vary the magnification or a non-continuously variable magnification optical lens having a plurality of fixed magnification lenses.

The displacement measurement means may comprise signal generation means for generating a position signal which varies with a change in the magnification of the variable magnification optical system, and signal detection means for detecting the position signal. The signal generation means may be arranged on the variable magnification optical system and the signal detection means may be arranged on the photographing device. When the photographing device is mounted on the viewing optical system, the signal generation means and the signal detection means may be coupled contactless. Accordingly, when the photographing device is attached or detached, the adjustment of the contact pressures of the signal generation means and the signal detection means is not necessary and it can be readily attached or detached.

In accordance with the present invention, the magnification is detected even in the variable magnification optical system which continuously varies the magnification, and the proper exposure for photographing is determined based on the magnification signal. In accordance with the present invention, when the photographing device is to be attached to the variable magnification optical system, it is not necessary to adjust parts of the magnification measurement means and the parts are not worn.

DETAILED DESCRIPTION OF THE PREFERRED EMBODIMENTS

One embodiment of the present invention is now explained with reference to the drawings.

Figure 1:
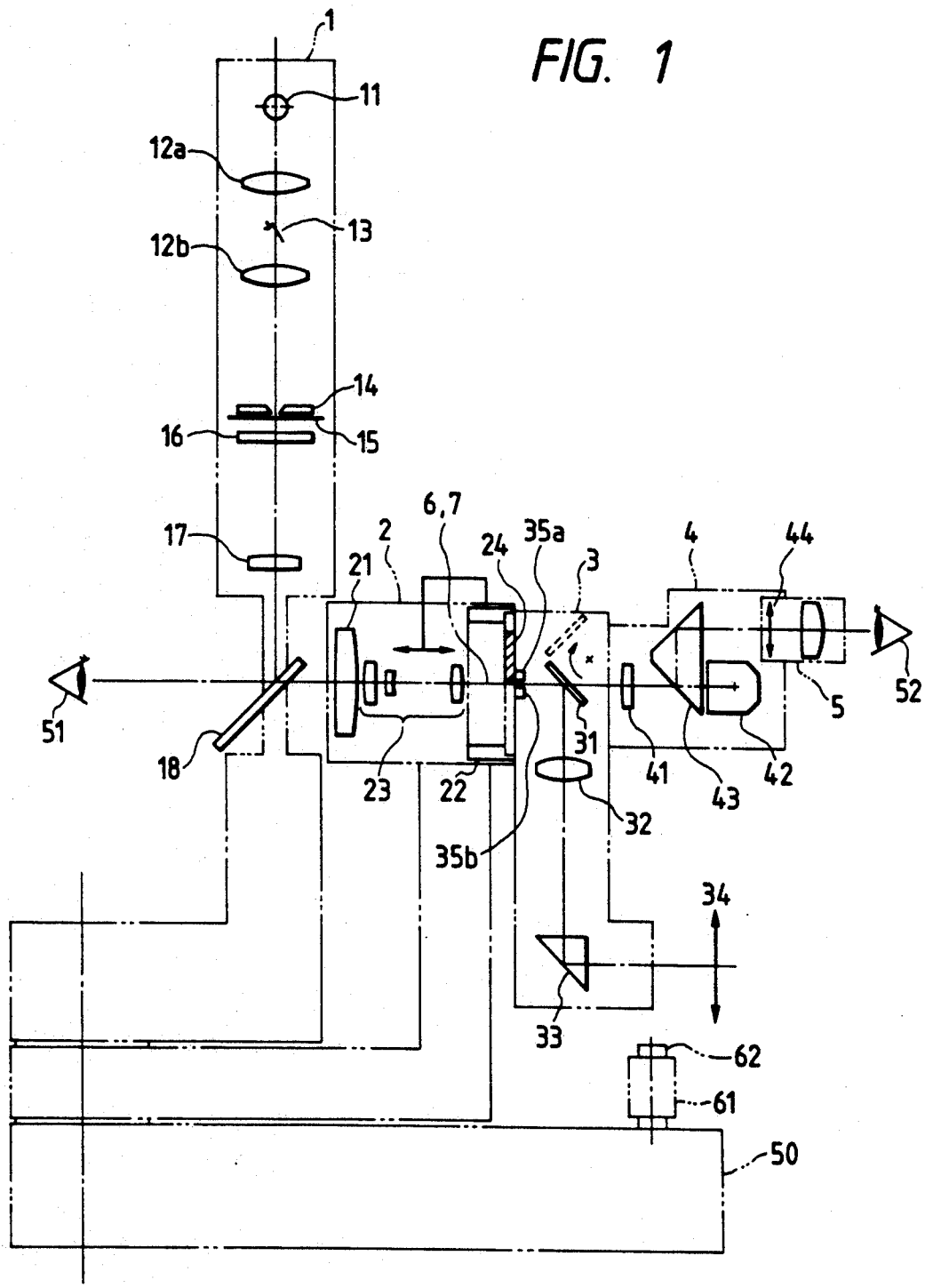
FIG. 1 shows one embodiment of an ophthalmic photographing apparatus of the present invention.
Figure 2:
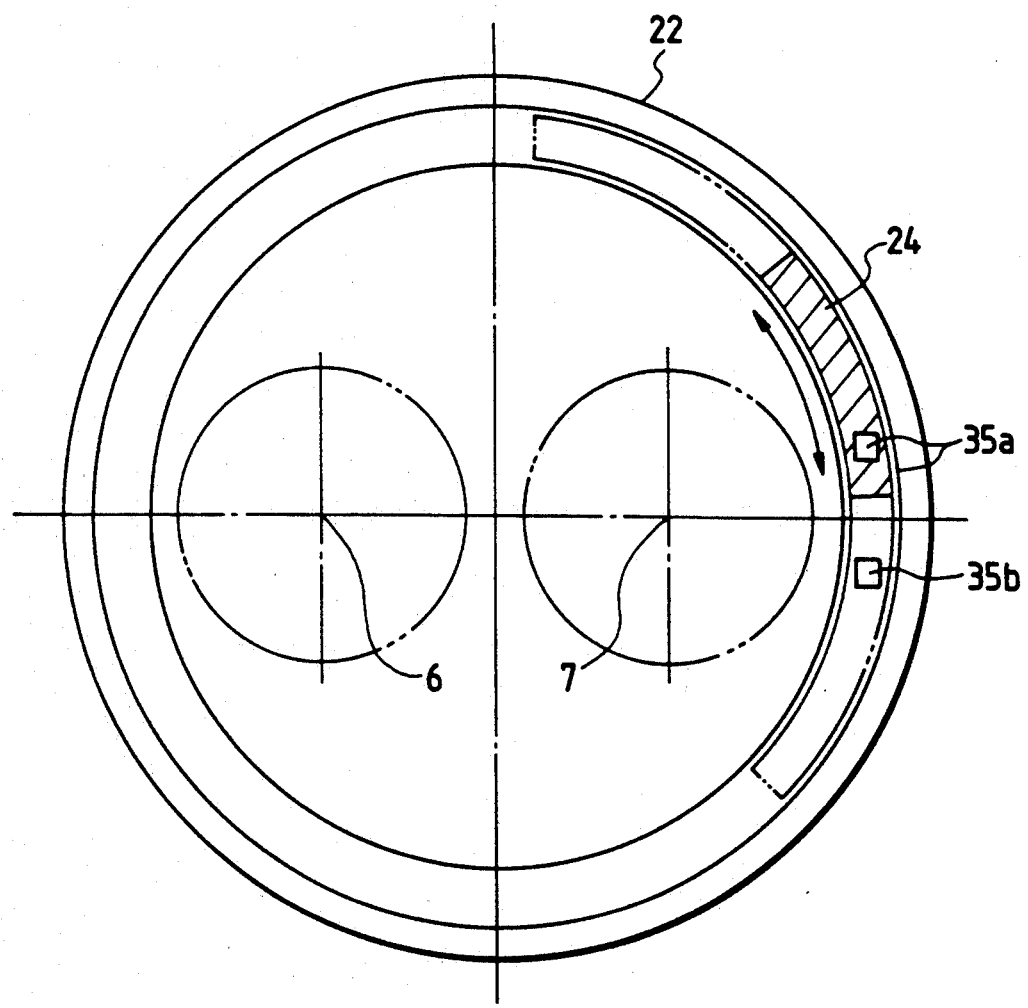
FIG. 2 shows an arrangement of a displacement measurement unit.
Figure 3:
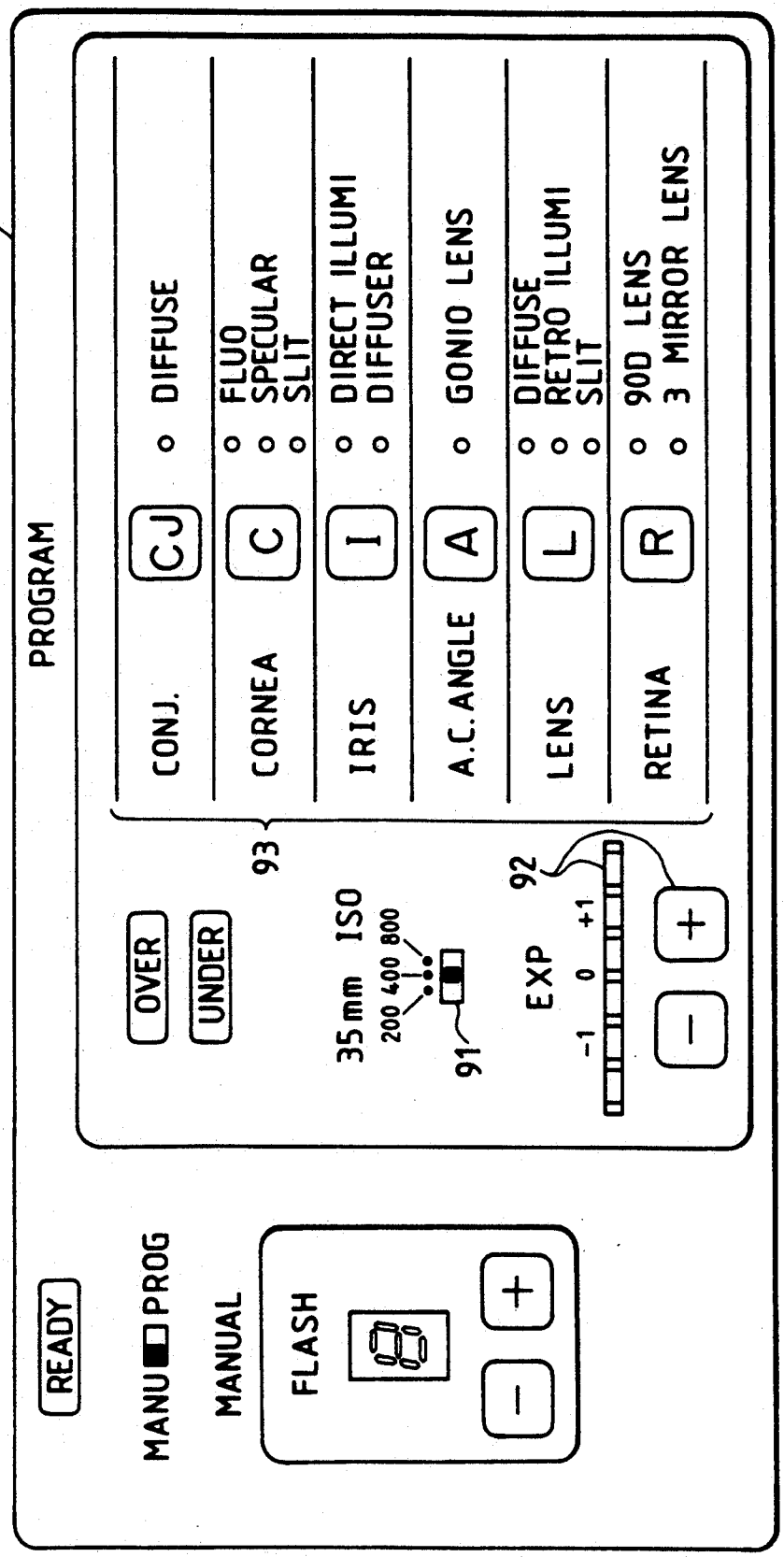
FIG. 3 shows a front view of a console panel for displaying photographing conditions.
Figure 4:
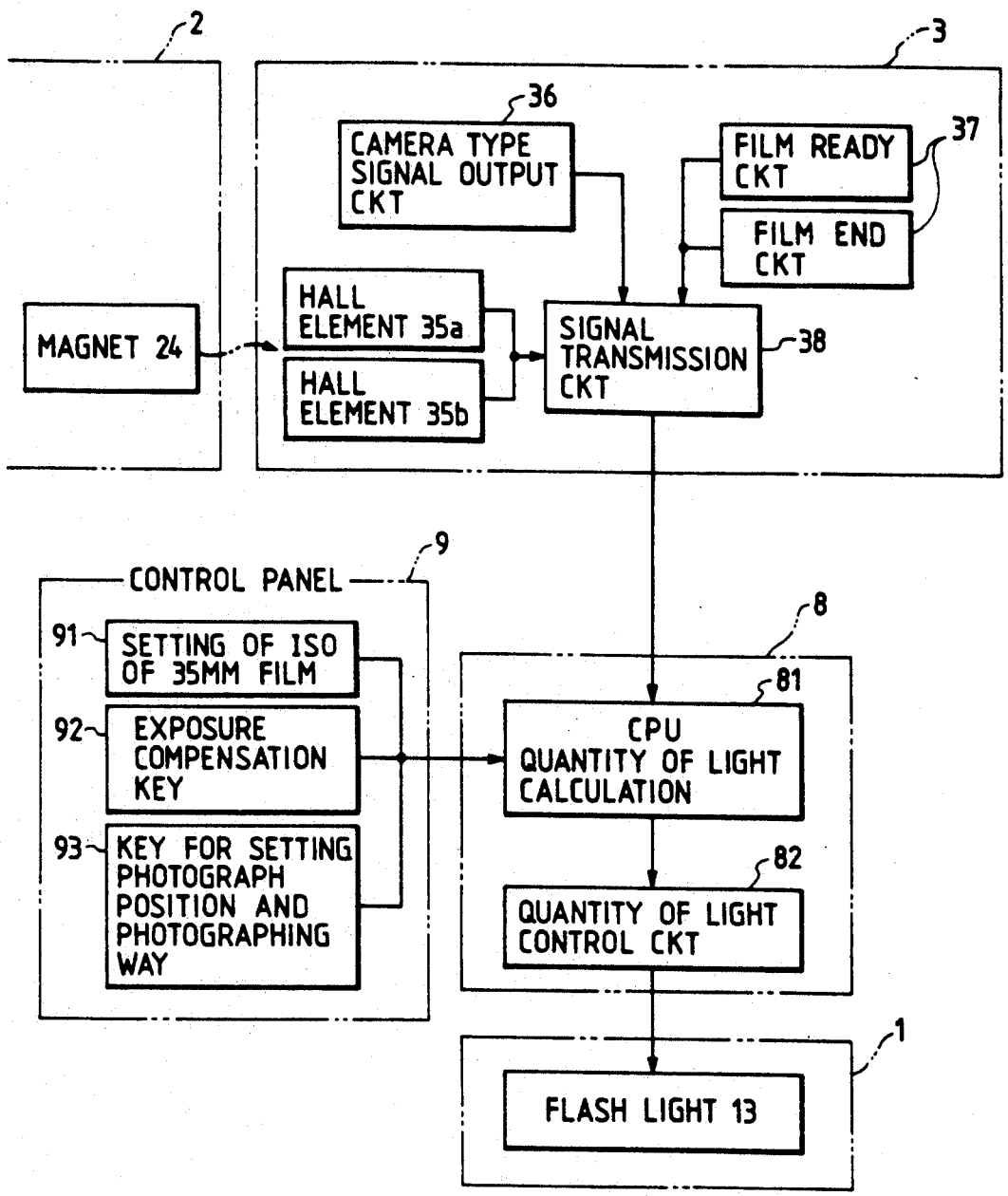
FIG. 4 shows a block diagram showing a flow of signal in stroboscope light intensity control.

FIG. 1 shows a light path chart of an ophthalmic photographing apparatus of the present invention, particularly a photo-slit lamp, FIG. 2 shows an arrangement of a displacement measurement unit, FIG. 3 shows a front view of a console panel which displays photographing conditions and FIG. 4 shows a block diagram which shows a process of stroboscope light intensity control.

In FIG. 1, numeral 1 denotes an illumination optical system, numeral 2 denotes a dual-eye viewing optical system, numeral 3 denotes a 35 mm camera photographing device, numeral 4 denotes a dual-eye lens barrel, numeral 5 denotes an eye lens, numeral 50 denotes a slip table, numeral 51 denotes an eye to be tested, numeral 52 denotes an eye of a viewer, numeral 61 denotes a joy stick lever and numeral 62 denotes a release switch.

The illumination optical system 1 is fixed on the slip table 50, and the dual-eye viewing optical system 2, the 35 mm camera photographing device 3, the dual-eye eye lens barrel 4 and the eye lens 5 are coupled in sequence to form a viewing photographing optical system, which is also mounted on the slip table 50.

The magnification of the dual-eye viewing optical system 2 is variable by a zoom lens 23 which is driven by the rotation of a magnification change ring 22. Numeral 24 (hatched area) denotes a magnet mounted on the magnification change ring 22 and it produces a signal representing the position of the magnification change ring.

Hall devices 35a and 35b are mounted on a mount of the 35 mm camera photographing device dual-eye viewing optical system. They are turned on and off by the presence or absence of a magnetic field. The Hall devices 35a and 35b face the magnet 24 on the magnification change ring 22 of the dual-eye viewing optical system 2 and they are turned on and off by the position of the magnet 24 on the magnification change ring 22.

Thus, the displacement of the magnification change ring 22 can be measured by the magnet 24 which generates a magnetic field and the Hall devices 35a and 35b which detect the magnetic field. The Hall devices 35a and 35b detect the magnetic field generated around the magnet 24 without contact between the magnet 24 and the Hall devices 35a and 35b. Accordingly, the magnet 24 and the Hall devices 35a and 35b are not worn. When the 35 mm camera photographing device is to be mounted on the dual-eye viewing optical system 2, it is not necessary to adjust the contact pressures between the magnet 24 and the Hall devices 35a and 35b, and it can be readily mounted.

FIG. 2 shows a positional relation of the magnet 24 and the Hall devices 35a and 35b, as viewed orthogonally to FIG. 1. When the magnet 24 mounted on the magnification change ring 22 is arcuately moved in association with the magnification change ring 22, the outputs of the Hall devices 35a and 35b are switched on and off to convert the position of the magnification change ring to an electrical signal. Since two Hall devices are used in the present apparatus, 2-bit signals or four different signals which represent the position of the magnification change ring 22 are generated by the combination of ON and OFF states of the Hall devices 35a and 35b by appropriately selecting the length of the magnet 24 and arranging the Hall devices 35a and 35b. Namely, as the magnet 24 passes over the Hall devices 35a and 35b, the signals generated by the Hall devices 35a and 35b are switched in the sequence of (0, 0), (1, 0), (1, 1) and (0, 1) in the combination of 35a and 35b.

FIG. 4 shows a block diagram which shows a process of transmitting the displacement signal of the variable magnification optical system and other photographing condition signals to a CPU to control the stroboscope light intensity.

In FIG. 4, numeral 8 denotes an exposure control unit which may be housed in a case of a power supply.

The 2-bit signal representing the position of the magnification change ring 22, which is detected by the Hall devices 35a and 35b in the photographing device 3 is sent to a signal transmission circuit 38 together with a signal from an output circuit 36 (35 mm camera photographing device) which represents the type of photographic recorder and a signal of a signal generator 37 (film ready circuit and film end circuit) which represents a status of film.

A CPU 81 in the exposure control unit 8 serially receives the signal outputted by the signal transmission circuit 38 of the photographing device 3. The CPU 81 also receives a signal from a film ISO setting key 91, a signal from an exposure correction key 92 and a signal from a key 93 for designating a photographed area and photographing manner, which are supplied from a console panel 9 arranged on the exposure control unit 8. When the CPU 81 receives those signals, it converts the signal representing the position of the magnet 24 of the magnification change ring 22 to a magnification signal which represents the magnification of the variable magnification optical system. It process the magnification signal together with the signals representing other photographing conditions to calculate a flash light intensity which is optimum to the photographing conditions.

A flash light intensity control circuit 82 receives the data for the flash light intensity calculated by the CPU 81 to cause the flash tube 13 in the illumination optical system 1 to emit a light.

FIG. 3 shows the console panel 9 which has the 35 mm film ISO setting key 91, the exposure correction key 92 and the key 93 for designating the photographed area and the photographing manner. The photographing condition may be set to a desired one by those keys.

A light path of the slit lamp microscope of the present embodiment and an operation thereof are explained below.

In the illumination optical system 1, the viewing illumination light irradiated from the viewing illumination light source 11 passes through a light source relay lens 12a and a light source relay lens 12b, the width thereof is adjusted by a variable width slit plate 14, and it passes through an illumination field ins 15, an exchangeable filter 16 and a relay lens 17, is deflected vertically by a reflection mirror 18 and illuminates the eye 51 to be tested. The flash tube 13 arranged in conjugation with the light source 11 emits a light only at the photographing and it serves as a photographing illumination light which follows the same light path as that of the viewing illumination light.

A reflected light from the eye 51 under test posses through an objective lens 21 of the dual-eye viewing optical system 2 and a zoom lens 23 which is driven by the rotation of the magnification change ring 22.

A quick return mirror 31 in the 35 mm camera photographing device 3 is linked to a release button 62 mounted on the joy stick 61 and it is inserted into the dual-eye viewing light paths 6 and 7 only at the photographing.

In the photographing mode, the light beam transmitted through the zoom lens 23 is deflected by the quick return mirror 31 in the 35 mm camera photographing device 3 and reaches to an image plane 34 as a photographing light beam through the relay lens 32 and the reflection prism 33.

In the non-photographing mode, the quick return mirror 31 is off the dual-eye viewing light paths 6 and 7 (shown by broken lines) so that the viewing light transmitted through the zoom lens 23 passes through the relay lens 41 in the dual-eye eye lens barrel 4, and is deflected by erection prisms 42 and 43 so that an image of the eye 51 under test is focused at 44. The image 44 of the eye under test is viewable by the eye 52 through the exchangeable eye lens 5.

The dual-eye viewing optical system 2, the 35 mm camera device 3 and the eye lens barrel 4 are detachable from each other so that other photographic recorder devices may be used or combined. The eye lens barrel 4 may be directly mounted on the viewing optical system 2. As shown in FIG. 4, the photographing device has the output circuit 36 to represent the type of photographing device and the signal generator 37 (film ready circuit and film end circuit) to represent the status of film.

As shown in FIG. 2, the magnet 24 and the Hall devices 35a and 35b are arranged at any positions which do not impede to the light beams of the dual-eye viewing optical paths 6 and 7 of the viewing optical system.

In FIG. 4, the console panel 9 does not have other ISO setting key than the 35 mm film setting key. Since it is assumed that a Polaroid standard film (ISO 600) is used in an instant photographing mode, ISO 600 is automatically set when an instant photographing device is mounted. ISO setting keys for the type of film may be provided as it is for the 35 mm film. The ISO for the 35 mm film is entered by the setting key on the console panel although the ISO may be automatically read from the film in a DX compatible camera.

In the present embodiment, the combination of the magnet and the Hall devices is used as non-contact signal transmission means although a photo-sensor such as a photo-interrupter may be used. Such a magnification measurement means does not need the adjustment of the contact pressures of the parts of the magnification measurement means and the parts are not worn.

The positions of the magnet 24 and the Hall devices 35 are adjustable to attain the exact operation. When three or more Hall devices are used, more magnification information is acquired. The magnification information may be displayed on a screen or in the viewing field.

In the present embodiment, the variable magnification optical system is a continuously variable magnification optical system although the present invention is equally applicable to a variable magnification optical system having a plurality of fixed magnification lenses. In this case, the position signal generation means such as Hall devices may be arranged on a revolver on which the fixed magnification lenses are mounted.

What is claimed is:

1. An ophthalmic photographing apparatus comprising:
    an illumination optical system for illuminating an eye to be tested;
    a viewing optical system having a variable magnification optical system for viewing the illuminated eye to be tested;
    a photographing device detachably mounted on said viewing optical system;
    displacement measurement means for measuring a displacement of a predetermined part due to the change of magnification of said variable magnification optical system; and
    signal output means for outputting a signal representing the displacement measured by said displacement measurement means.

2. An ophthalmic photographing apparatus according to claim 1 wherein said displacement measurement means includes position signal generation means for generating a varying position signal in accordance with the change of magnification of said variable magnification optical system and position signal detection means for detecting the position signal, said position signal generation means is arranged in said viewing optical system, and said position signal detection means is arranged in said photographing device.

3. An ophthalmic photographing apparatus according to claim 2 wherein said signal generation means and said signal detection means do not contact to each other when said photographing device is mounted on said viewing optical system.

4. An ophthalmic photographing apparatus according to claim 2 wherein said photographing device includes signal conversion means for converting the signal detected by said signal detection means to a signal representing the magnification of said variable magnification optical system.

5. An ophthalmic photographing apparatus according to claim 2 wherein said signal generation means is magnetic field generation means.

6. An ophthalmic photographing apparatus according to claim 5 wherein said magnetic field generation means is mounted on a ring for varying the magnification of said variable magnification optical system by mechanically displacing said variable magnification optical system.

7. An ophthalmic photographing apparatus according to claim 2 wherein said signal generation means includes a magnet and said signal detection means includes a Hall device.

8. An ophthalmic photographing apparatus according to claim 1 further comprising exposure control means for controlling an exposure condition in photographing by said photographing device based on the signal produced by said signal output means.

9. An ophthalmic photographing apparatus of claim 8 further comprising a flash light for illuminating the eye to be tested at the photographing wherein said exposure control means control a light intensity of said flash light.

10. An ophthalmic photographing apparatus according to claim 8 further comprising means for setting an ISO sensitivity of a photographing film to said exposure control means.

11. An ophthalmic photographing apparatus according to claim 8 further comprising means for setting an exposure correction at the photographing to said exposure control means.

12. An ophthalmic photographing apparatus according to claim 1 wherein said predetermined part is a ring for varying the magnification of said variable magnification optical system by mechanically displacing said variable magnification optical system.

* * * * *